US00PP11918P2

(12) United States Plant Patent
Glicenstein

(10) Patent No.: US PP11,918 P2
(45) Date of Patent: Jun. 12, 2001

(54) CHRYSANTHEMUM PLANT NAMED 'HOT SALSA'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/225,017

(22) Filed: Jan. 4, 1999

(51) Int. Cl.[7] ..... A01H 5/00
(52) U.S. Cl. ..... Plt./298
(58) Field of Search ..... Plt./286, 298

(56) References Cited

U.S. PATENT DOCUMENTS

P.P. 9,578 * 6/1996 Fuess ..... Plt./286
4,616,099 * 10/1986 Sparkes ..... 47/58

OTHER PUBLICATIONS

Broertjes, et al., 1980, "A mutant of a . . . Irradiation of progressive radiation–induced mutants is a mutation breeding programme with *Chrysanthemum morifolium*", Euphytica, 29:525–530.*
Gosling, ed., 1979, "Chrysanthemum Manual—6th edition", The National Chrysanthemum Society, London, Essex Telegraph Press, Ltd., pp. 329–336.*
Broertjes, et al., 1978, "Application of Mutation Breeding Methods in the Improvement of Vegetativily Propagated Crops", Elsevier Sci. Pub. Co., New York, pp. 162–175.*
Searle, et al., 1968, "Chrysanthemums the Year Round", Blanford Press, London, pp. 27–29, 320–327.*
Chan, 1966, "Chrysanthemum and rose mutations induced by X–rays", Am. Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in chrysanthemum using X– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Hot Salsa', characterized by its uniformly mounded plant habit; daisy-type inflorescences that are about 5.4 cm in diameter; attractive bright red ray florets and bright yellow disc florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Hot Salsa.

The new cultivar is a product of a mutation induction breeding program conducted by the inventor in Fort Myers, Fla., and Salinas, Calif. The objective of the breeding program is to create new garden-type Chrysanthemum cultivars having with desirable inflorescence form and color and good garden performance.

The new cultivar originated by exposing unrooted cuttings of the Chrysanthemum cultivar Empire Salsa (disclosed in U.S. Plant Pat. No. 9,578) to X-ray radiation at a level of 2,000 rads in February, 1994. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar Hot Salsa was discovered and selected by the inventor as a single flowering plant within this population in May, 1995. The selection of this plant was based on its desirable ray floret color.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Hot Salsa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Hot Salsa'. These characteristics in combination distinguish 'Hot Salsa' as a new and distinct cultivar:

1. Uniformly mounded plant habit.

2. Daisy-type inflorescences that are about 5.4 cm in diameter.

3. Attractive bright red ray and bright yellow disc florets.

4. Numerous inflorescences per plant.

The new Chrysanthemum is similar to the parent cultivar Empire Salsa. However in side-by-side comparisons under commercial practice, plants of the new Chrysanthemum differed from plants of the cultivar Empire Salsa in the following characteristics:

1. Plants of the new Chrysanthemum flower a few days earlier than plants of the cultivar Empire Salsa under natural season conditions.

2. Plants of the new Chrysanthemum have larger inflorescences than plants of the cultivar Empire Salsa.

3. Ray florets of plants of the new Chrysanthemum are bright red in color whereas ray florets of plants of the cultivar Empire Salsa are reddish purple in color.

4. Plants of the new Chrysanthemum are more compact than plants of the cultivar Empire Salsa.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Hot Salsa'.

The photograph at the bottom of the sheet comprises a close-up view of typical inflorescences of the cultivar 'Hot Salsa'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Hot Salsa.

Commercial classification: Daisy-type garden chrysanthemum.

Parentage: Induced mutation of *Dendranthema grandiflora* cultivar Empire Salsa, disclosed in U.S. Plant Pat. No. 9,578.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 8 laterals develop.

*Plant height.*—About 31 cm.

*Plant spread.*—About 48 cm.

*Foliage description.*—Leaf arrangement: Alternate. Length: About 5.75 cm. Width: About 5.6 cm. Apex: Cuspidate to mucronate. Base: Typically truncate. Margin: Palmately lobed, sinuses typically divergent. Texture: Upper surface sparsely pubescent; lower surface moderately pubescent. Veins prominent on lower surface. Petiole length: About 2.5 cm. Petiole diameter: About 3 mm. Color: Young foliage upper surface: Darker than 147A. Young foliage lower surface: Darker than 147B. Mature foliage upper surface: 147A. Mature foliage lower surface: 147B. Venation upper surface: 147A/147B. Venation lower surface: 147B.

Inflorescence description:

*Appearance.*—Daisy-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant, about 9 per lateral stem.

*Flowering response.*—Under natural season conditions, plants flower in late September in the Northern Hemisphere, about 79 days after planting, and flower for at least three weeks depending on weather conditions.

*Inflorescence bud (before showing color).*—Height: About 6 mm. Diameter: About 8.5 mm. Phyllary color: Darker than 146A.

*Inflorescence size.*—Diameter: About 5.4 cm. Depth (height): About 1.4 cm. Diameter of disc: About 1.6 cm.

*Ray florets.*—Shape: Oblong, convex; longitudinally ridged. Length: About 2.5 cm. Width: About 7 mm. Apex: Dentate. Margin: Entire. Texture: Smooth, glabrous. Orientation: Initially upright, then horizontal. Number of ray florets per inflorescence: About 74. Color: When opening: Upper surface: 46A to slightly darker than 46A. Lower surface: Close to 46A, dull. Opened inflorescence: Upper surface: 46A to 45A; fading to dulled 46A. Lower surface: Close to 46A, dull.

*Disc florets.*—Shape: Tubular, apex dentate. Length: About 5.5 mm. Width: Apex: About 2 mm. Base: About 1 mm. Number of disc florets per inflorescence: Typically more than 150. Color: Immature: 154A. Mature: Apex: 9A. Mid-section: Light green. Base: White.

*Peduncle.*—Aspect: Flexible, angled about 50° to the stem. Length: First peduncle: About 8.2 cm. Fourth peduncle: About 10.4 cm. Diameter: About 2 mm. Texture: Pubescent. Color: Close to 147A.

*Reproductive organs.*—Androecium: Present on disc florets only. Anther color: 9A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Hot Salsa', as illustrated and described.

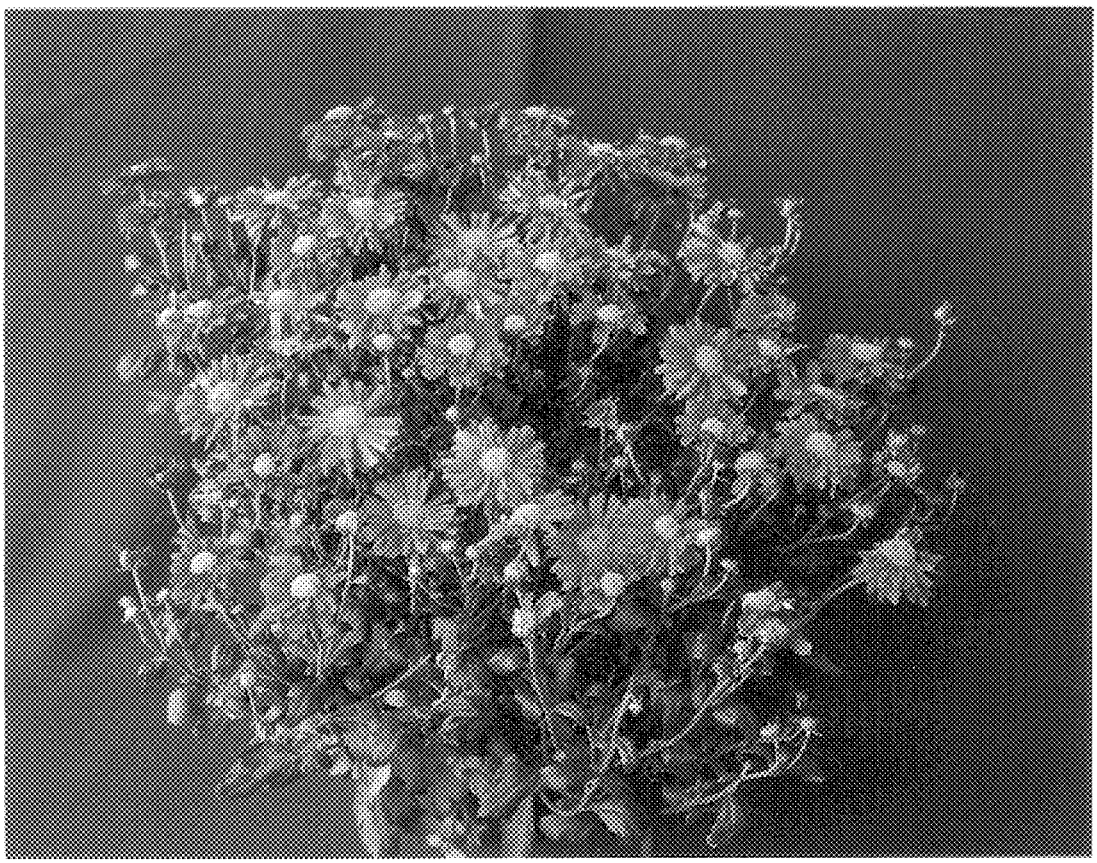
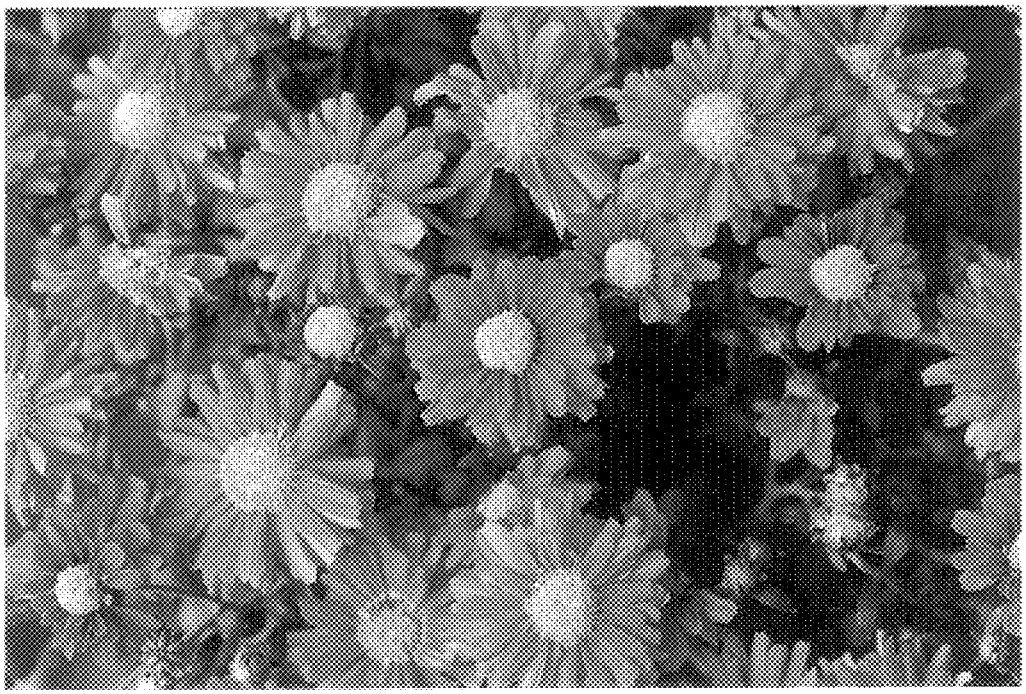

* * * * *